United States Patent [19]

Ryan

[11] Plant 4,410

[45] Apr. 24, 1979

[54] IMPATIENS PLANT — OSAGE

[76] Inventor: John J. Ryan, 39877 Sundale Dr., Fremont, Calif. 94538

[21] Appl. No.: 921,889

[22] Filed: Jul. 3, 1978

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant, known by the cultivar name OSAGE, and discovered by me in commercial greenhouses in Fremont, Calif. OSAGE is closest in characteristics to Longwood's CAROUSEL, but is particularly characterized by its much larger flower, larger leaves, longer internodes, and more consistent flowering.

1 Drawing Figure

BACKGROUND OF THE INVENTION

The present new variety (seedling) was discovered by me in a commercial greenhouse in Fremont, Calif. as a result of the cross pollination of the patented pistil parent 76-2-1 (CREEK) U.S. Plant Pat. No. 4,261 and the unpatented pollen parent 75-34.

Asexual reproduction of my new cultivar by terminal or stem cuttings grown in pots in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

OSAGE is closest in characteristics to Longwood's CAROUSEL. The following outstanding characteristics of OSAGE distinguish it from Longwood's CAROUSEL:

1. OSAGE has a much larger flower;
2. Although variegation is similar, OSAGE has a larger leaf;
3. OSAGE has longer internodes with a very upright form, making an excellent pot type plant;
4. OSAGE flowers more consistently; CAROUSEL can be difficult to get to flower.

DESCRIPTION OF PHOTOGRAPH

The accompanying colored photograph illustrates the overall appearance of the cultivar OSAGE, showing a flower color slightly darker than usual. Under high light the flower color goes from a red-orange to orange.

DETAILED DESCRIPTION

The following detailed description of OSAGE was based on observations made of the new cultivar on Oct. 26, 1977 and Nov. 1, 1977.

I. PLANT

Name: OSAGE.
Origin: Seedling of the cross pollination of the patented pistil parent 76-2-1 (CREEK) U.S. Plant Pat. No. 4,261 and the unpatented pollen parent 75-34.

Form: Upright.
Height to flowering: 45 cm.
Growth: Fast.
Type of cutting: Terminal or stem.
Rooting time: Typical, 10–14 days.
Rooting habit: Fast, dendritic.

II: Foliage

Arrangement: Lower leaves of any break opposite; (usually one set) upper foliage of any break whorls of 3 and 4.
Shape: Oblanceolate to lanceolate.
Tip: Acuminate.
Base: Attenuate.
Margin: Serrulate.
Veination: Pinnate.
Size: Blade and petiole 15.5 cm. to 22.0 cm.; length of blade 12.5 cm to 17.0 cm.; width of blade at widest point 3.5 cm. to 5.5 cm.
Surface: Glabrous and glossy.
Variegation: High light increases the variegation width; low light reduces it.
Color:

1. *Petiole.*—53 D.
2. *Veins.*—Lower surface 139 D, upper surface grades into variegation.
3. *Leaf.*—a. Upper: 137 A to 137 B. b. Lower: 139 D.
4. *Variegation.*—a. Edge: 137 A to 137 B. b. Middle: 18 B, reddening along middle especially under high light. c. Center: 18 B.

III. STEM

Color: 53 B.
Internode:

1. *Length.*—Moderate to long.
2. *Size.*—Moderate.

Node expanded (relative to internode): Slightly expanded.
Breaking action: Moderate to good.

IV. FLOWER

Form: Typical.
Borne: End of branches, terminal.
Blooming habit:

1. *Relative number.*—Moderate.
2. *Time to flowering.*—Moderate.

3. *Longevity.*—Typical, 3 to 5 days.

Size of Mature Flower: First flower on a plant may be small.

1. *Length.*—5.5 cm. to 6.5 cm.
2. *Width.*—6.0 cm to 7.0 cm.
3. *Spur.*—4.5 cm. to 5.5 cm.

Color: Light red-orange to orange under high light and heat

| | |
|---|---|
| 1. Eye: | 46 C |
| 2. Middle | 33 A |
| 3. Edge | 33 A |

*Pedicel.*—53 C.

V. REPRODUCTIVE ORGANS

Stamen:

| | |
|---|---|
| 1. Anthers | Typical, fused hood over pistil |
| 2. Filaments | Typical, fused hood over pistil |

3. *Pollen.*—a. Color: 158 B. b. Abundance: Typical, plenty.

Pistils:

| | |
|---|---|
| 1. Style | Typical |
| 2. Ovaries | Typical |

VI. OTHER CHARACTERISTICS

The heavy stem growth of OSAGE should withstand most weather conditions when OSAGE is used as a bedding plant.

I claim:

1. A new and distinct form of Impatiens plant, as described and illustrated, known by the cultivar name OSAGE, and particularly characterized by a large orange flower, large variegated leaves, a stiff upright growth habit, and a more consistent flowering habit than Longwood's CAROUSEL.

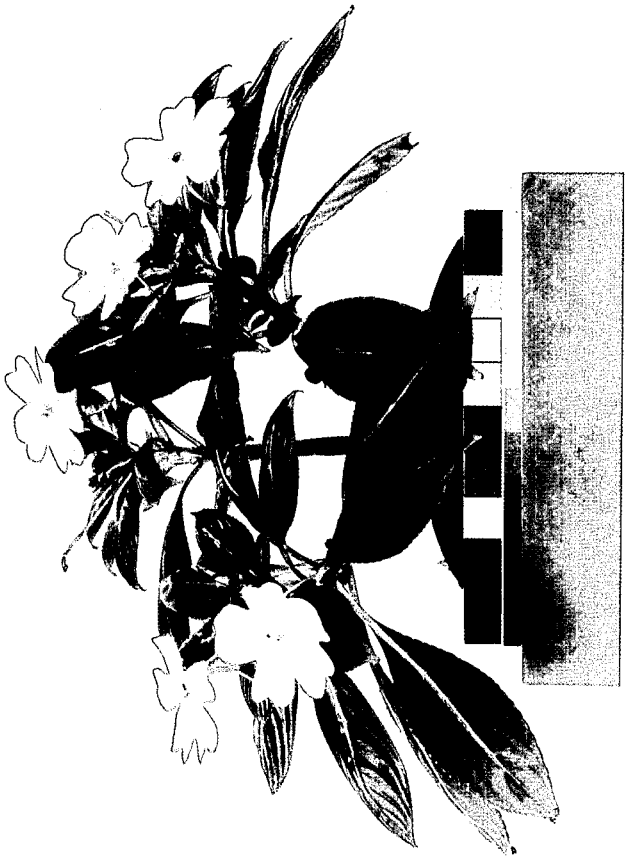

* * * * *